(12) United States Patent
Cannell et al.

(10) Patent No.: US 7,431,937 B2
(45) Date of Patent: Oct. 7, 2008

(54) COMPOSITIONS COMPRISING AT LEAST ONE AMINATED C5-C7 SACCHARIDE UNIT, AND THEIR USE FOR THE PROTECTION AND/OR REPAIR OF KERATINOUS FIBERS

(75) Inventors: David W. Cannell, Plainfield, NJ (US); Natalya Fadeeva, Clark, NJ (US); Nghi Van Nguyen, Edison, NJ (US)

(73) Assignee: L'Oreal, S.A., Paris (FR)

( * ) Notice: Subject to any disclaimer, the term of this patent is extended or adjusted under 35 U.S.C. 154(b) by 789 days.

(21) Appl. No.: 09/820,954

(22) Filed: Mar. 30, 2001

(65) Prior Publication Data

US 2003/0053977 A1    Mar. 20, 2003

(51) Int. Cl.
A61K 8/02    (2006.01)
(52) U.S. Cl. .................. 424/401; 514/836; 514/938
(58) Field of Classification Search ................ 424/70.9, 424/400–401; 514/62
See application file for complete search history.

(56) References Cited

U.S. PATENT DOCUMENTS

| 4,900,545 | A |   | 2/1990  | Wisotzki et al.          |
|-----------|---|---|---------|--------------------------|
| 5,141,964 | A | * | 8/1992  | Noel .............. 252/8.63 |
| 5,348,737 | A |   | 9/1994  | Syed et al.              |
| 5,641,477 | A |   | 6/1997  | Syed et al.              |
| 5,660,838 | A |   | 8/1997  | Koga et al.              |
| 5,679,344 | A | * | 10/1997 | Williams et al. ..... 424/451 |
| 5,866,142 | A | * | 2/1999  | Riordan ............. 424/401 |
| 5,888,951 | A |   | 3/1999  | Gagnebien et al.         |

FOREIGN PATENT DOCUMENTS

| DE | 297 09 853  |   | 11/1998 |
|----|-------------|---|---------|
| JO | 06-122614   |   | 5/1994  |
| JP | 04-266812   |   | 9/1992  |
| JP | 09-059134   |   | 3/1997  |
| JP | 10-279439   |   | 10/1998 |
| WO | WO 01/93831 | * | 12/2001 |

OTHER PUBLICATIONS

Merck Index 7th ed. 1989, 4675, pp. 751-752.*
Milczarek et al., "The Mechanism and Stability of Thermal Transitions in Hair Keratin", *Colloid and Polymer Science*, vol. 270, No. 11, 1992, pp. 1106-1115.
Hollenberg et al., "Möglichkeiten Zur Beeinflussing Der Haarstruktur Durch Pflegeprodukte", *SÖFW-Journal*, vol. 121, No. 2, 1995, pp. 82-89.
ACS Abstract 123:296216 CA: Hollenberg et al., *SÖFW-Journal*, vol. 121, No. 2, 1995, pp. 82-89.
Hollenberg et al., "Möglichkeiten Zur Beeinflussing Der Haarstruktur Mit Kosmetischen Mittein", *Seifen—Öle—Fette—Wachse*, vol. 117, Jan. 1991, pp. 9-18.
ACS Abstract 114:149908 CA: Hollenberg et al., *Seifen—Öle—Fette—Wachse*, vol. 117, Jan. 1991, pp. 9-18.

Spei et al., "Thermoanalytical Investigations of Extended and Annealed Keratins", *Colloid & Polymer Science*, vol. 265, No. 11, 1987, pp. 965-970.
Sandhu et al., "A Simple and Sensitive Technique, Based on Protein Loss Measurements, to Assess Surface Damage to Human Hair", *J. Soc. Cosmet. Chem*, vol. 44, No. 3, May/Jun. 1993, pp. 163-175.
Results from literature search performed by Assignee, 11 pages, May 20, 1999.
Results from literature search performed by Assignee, 24 pages, Nov. 17, 1999.
English language Derwent Abstract of DE 297 09 853, Sep. 20, 1994.
English language Derwent Abstract of JP 06-122614, May 6, 1994.
English language Derwent Abstract of JP 04-266812, Sep. 22, 1992.
English language Derwent Abstract of JP 10-279439, Oct. 20, 1998.
English language Derwent Abstract of JP 09-059134, Mar. 4, 1997.
Co-pending Application, Compositions Comprising at Least One Aminated $C_5$-$C_7$ Saccharide Unit, and Their Use for the Protection and/or Repair of Keratinous Fibers, David W. Cannell et al, filed Mar. 30, 2001.
Co-pending Application, Compositions Comprising at Least One Compound the USe of $C_3$-$C_5$ Monosaccharides to Protect Keratinous Fibers, David W. Cannell et al., filed Jul. 11, 2000.
Co-pending Application, Heat Activated Durable Styling Compositions Comprising $C_3$-$C_5$ Monosaccharides and Methods for Same, David W. Cannell et al., filed Mar. 30, 2001.
Co-pending Application, Compositions Comprising at Least One $C_1$ to $C_{22}$ Substituted C3 to $C_5$ Monosaccharide , and Their Use for the Protection and/or Repair of Keratinous Fibers, David W. Cannell et al., filed Mar. 30, 2001.
Co-pending Application, Heat Activated Durable Styling Compositions Comprising Aminated $C_5$ to $C_7$ Saccharide Units and Methods for Same, David W. Cannell et al., filed Mar. 30, 2001.
Co-pending Application, Heat Activated Durable Conditioning Compositions Comprising an Aminated $C_5$ to $C_7$ Saccharide Unit and Methods for Using Same, David W. Cannell et al., filed Mar. 30, 2001.
Co-pending Application, Heat Activated Durable Styling Compositions Comprising $C_1$ to $C_{22}$ Substituted $C_3$-$C_5$ Monosaccharides and MEthods for Same, David W. Cannell et al., filed, Mar. 30, 2001.
Co-pending Application, Heat Activated Durable Conditioning Comprising $C_1$ to $C_{22}$ Substituted $C_3$-$C_5$ Monosaccharides and Methods for Same, David W. Cannell et al., filed Mar. 30, 2001.

* cited by examiner

*Primary Examiner*—Sreeni Padmanabhan
*Assistant Examiner*—Layla Soroush
(74) *Attorney, Agent, or Firm*—Finnegan Henderson Farabow Garrett & Dunner, L.L.P.

(57) ABSTRACT

Compositions, optionally heat-activated, methods and kits for protecting keratinous fibers from extrinsic damage or repairing keratinous fibers damaged by extrinsic conditions by applying to keratinous fibers a composition comprising at least one compound comprising at least one $C_5$ to $C_7$ saccharide unit substituted with at least one amino group and derivatives thereof, and heating the keratinous fibers.

2 Claims, 1 Drawing Sheet

COMPOSITIONS COMPRISING AT LEAST ONE AMINATED C5-C7 SACCHARIDE UNIT, AND THEIR USE FOR THE PROTECTION AND/OR REPAIR OF KERATINOUS FIBERS

The present invention relates to compositions, kits comprising these compositions, and methods for using these compositions for repairing or for protecting from extrinsic damage at least one keratinous fiber, including human keratinous fibers, by applying to the at least one keratinous fiber compositions which comprise at least one compound comprising at least one $C_5$ to $C_7$ saccharide unit substituted with at least one amino group, and heating the keratinous fibers. These compositions may both protect and repair the keratinous fibers.

Keratinous fibers, and especially hair, are constantly exposed to harsh extrinsic conditions such as sun (i.e., UV radiation), chemical damage (for example, from detergents, bleaching, relaxing, dyeing, and permanent waving), and heat (for example, from hair dryers or curlers). These external factors generally result in damage to the keratinous fibers. More specifically, extrinsic conditions may disrupt the organized structure of the keratinous fibers, called the α-structure, which may be accompanied by a decrease in their tensile strength. The extrinsic damage to keratinous fibers, as one would imagine, is more evident the further the fiber has grown from the root, because the fiber has been exposed longer to the elements. In effect, the fibers have what may be called a "damage history" as they grow, i.e., generally, further from the root, the tensile strength of the fiber is lower and the breakdown in the α-structure of the fiber that has occurred is greater.

Morphologically, a keratinous fiber contains four structural units: cuticle, cortex, medulla, and intercellular cement. Robbins, C. R. *Chemical and Physical Behavior of Human Hair*, 3$^{rd}$ Edition, Springer-Verlag (1994). The cuticle layers are located on the fiber surface and consist of flat overlapping cells ("scales"). These scales are attached at the root end and point toward the distal (tip) end of the fiber and form layers around the fiber cortex. The cortex comprises the major part of the fiber. The cortex consists of spindle-shaped cells, macrofibrils, that are aligned along the fiber axis. The macrofibrils further consist of microfibrils (highly organized protein units) that are embedded in the matrix of amorphous protein structure. The medulla is a porous region in the center of the fiber. The medulla is a common part of wool fibers but is found only in thicker human keratinous fibers. Finally, the intercellular cement is the material that binds the cells together, forming the major pathway for diffusion into the fibers.

The mechanical properties of the keratinous fibers are determined by the cortex. A two-phase model for the cortex organization has been suggested. Milczarek et al, *Colloid Polym. Sci.*, 270, 1106-1115 (1992). In this model, water-impenetrable microfilaments ("rods") are oriented parallel with the fiber axis. The microfilaments are embedded in a water-penetrable matrix ("cement"). Within the microfilaments, coiled protein molecules are arranged in a specific and highly organized way, representing a degree of crystallinity in the fiber.

Similar to other crystalline structures, keratinous fibers display a distinct diffraction pattern when examined by wide-angle X-ray diffraction. In normal, non-stretched keratinous fibers this pattern is called an "alpha-pattern". The alpha-pattern or α-structure of hair is characterized by specific repeated spacings (9.8 Å, 5.1 Å, and 1.5 Å). All proteins that display this X-ray diffraction pattern are called α-proteins and include, among others, human hair and nails, wool, and porcupine quill. When the fiber is stretched in water, a new X-ray diffraction pattern emerges that is called a "β-pattern", with new spacings (9.8 Å, 4.65 Å, and 3.3 Å).

It is the α-structure of the cortex of the fiber that is sensitive to damage by extrinsic conditions. When normal keratinous fibers are damaged by heat, chemical treatment, or UV radiation, a decrease in the crystallinity or α-structure and a decrease in the number of disulfide bonds are observed. There is a need, therefore, for products that are useful in protecting the α-structure of keratinous fibers from harsh extrinsic conditions and restoring the α-structure following damage by extrinsic conditions.

The aforementioned products are, for example, cosmetic compositions containing sugars. Sugars and sugar derivatives are one class of the countless number of compounds that have been added to hair care compositions. Documented uses of sugars in hair care compositions include: the use of glucose to improve the tactile and elastic properties of natural hair (Hollenberg and Mueller, *SOFW J.* 121(2) (1995)); the use of glucose for hair damage prophylaxis and damaged hair repair (Hollenberg & Matzik, *Seifen, Oele, Fette, Wachase* 117(1) (1991)); the use of glucose in shampoos (J04266812, assigned to Lion Corp.); the use of trehalose for moisture retention (J06122614, assigned to Shiseido Co. Ltd.); a composition for the lanthionization of hair comprising a sugar (U.S. Pat. Nos. 5,348,737 and 5,641,477, assigned to Avlon Ind. Inc.); the incorporation of xylobiose into cosmetic compositions to provide enhanced moisture retention and reduce excessive roughness and dryness of the skin and hair (U.S. Pat. No. 5,660,838, assigned to Suntory Ltd.); a composition for the regeneration of hair split-ends that contains at least one mono- or di-saccharide (U.S. Pat. No. 4,900,545, assigned to Henkel); hair care compositions to improve hair strength, hold and volume that contain $C_5$ to $C_6$ carbohydrates such as glucose; the use of fucose in a hair treatment to prevent split ends (DE29709853, assigned to Goldwell GMBH); and the use of saccharides in a shampoo to improve combing properties and control hair damage (J09059134, assigned to Mikuchi Sangyo KK).

In essence, sugars have been applied to hair for countless reasons from moisturizing to enhancing hair growth (J10279439, assigned to Kureha Chem. Ind. Co. Ltd.). Clearly, however, not all sugars are the same and not all sugars impart the same properties when applied to a keratinous fiber. Additionally, the use of specific sugars that protect hair from extrinsic damage and, more particularly, protect the α-structure of hair from such damage has not been demonstrated. As a result, if sugars are going to be useful in protecting hair from extrinsic damage, a better understanding of the advantages of using sugars in hair care compositions is needed, and more specifically, an understanding of how sugars may be useful in restoring and protecting keratinous fibers.

The inventors have envisaged the application to at least one keratinous fiber of at least one composition comprising at least one compound comprising at least one $C_5$ to $C_7$ saccharide unit substituted with at least one amino group. In particular, the inventors have discovered that compositions and methods using these compositions comprising applying to the at least one keratinous fiber at least one composition comprising at least one compound comprising at least one $C_5$ to $C_7$ saccharide unit substituted with at least one amino group, and heating the at least one keratinous fiber are useful for repairing or for protecting from extrinsic damage the at least one keratinous fiber.

Thus, to achieve at least one of these and other advantages, the present invention, in one aspect, provides a method for protecting at least one keratinous fiber from extrinsic damage or repairing at least one keratinous fiber following extrinsic damage comprising applying to the at least one keratinous fiber a composition comprising at least one compound comprising at least one $C_5$ to $C_7$ saccharide unit substituted with at least one amino group; and heating the at least one keratinous fiber, wherein the at least one compound is present in an amount effective to protect the at least one keratinous fiber from the extrinsic damage or to repair a damaged keratinous fiber, and further wherein the composition is applied prior to or during the heating.

In another embodiment, the present invention relates to compositions for protecting at least one keratinous fiber from extrinsic damage or for repairing at least one keratinous fiber following extrinsic damage comprising at least one compound comprising at least one $C_5$ to $C_7$ saccharide unit substituted with at least one amino group, wherein the at least one compound is present in an amount effective to protect the at least one keratinous fiber from the extrinsic damage or to repair a damaged keratinous fiber. In one embodiment, the composition is heat-activated.

In yet another embodiment, the present invention provides a kit for protecting at least one keratinous fiber from extrinsic damage or for repairing at least one keratinous fiber following extrinsic damage comprising at least one compartment, wherein a first compartment comprises a first composition comprising at least one compound comprising at least one $C_5$ to $C_7$ saccharide unit substituted with at least one amino group. In one embodiment, at least one compartment comprises at least one additional sugar, different from the at least one compound.

Certain terms used herein are defined below:

"Extrinsic damage" as used herein means disruption of the α-structure, protein loss, and/or denaturing caused by exposure to extrinsic conditions.

"Extrinsic conditions" as used herein means heat (such as from hair dryers or curlers), chemicals (such as those used in detergents, bleaching, relaxing, dyeing, and permanent waving), and/or UV radiation (such as, for example, from light sources).

"At least one" as used herein means one or more and thus includes individual components as well as mixtures/combinations.

"Heating" refers to the use of elevated temperature (i.e., above 100° C). In one embodiment, the heating in the inventive method may be provided by directly contacting the at least one keratinous fiber with a heat source, e.g., by heat styling of the at least one keratinous fiber. Non-limiting examples of heat styling by direct contact with the at least one keratinous fiber include flat ironing, and curling methods using elevated temperatures (such as, for example, setting hair in curlers and heating, and curling with a curling iron and/or hot rollers). In another embodiment, the heating in the inventive method may be provided by heating the at least one keratinous fiber with a heat source which may not directly contact the at least one keratinous fiber. Non-limiting examples of heat sources which may not directly contact the at least one keratinous fiber include blow dryers, hood dryers, heating caps and steamers.

"A heat-activated" composition, as used herein, refers to a composition which, for example, protects the at least one keratinous fiber better than the same composition which is not heated during or after application of the composition. Another example includes a composition which repairs the at least one keratinous fiber better than the same composition which is not heated during or after application.

"Keratinous fibers" as defined herein may be human keratinous fibers, and may be chosen from, for example, hair.

"Oligosaccharides" as defined herein refers to compounds generally comprising from two to ten monosaccharide units, which may be identical or different, bonded together.

"Polysaccharides" as defined herein refers to compounds generally comprising greater than ten monosaccharide units, which may be identical or different, bonded together.

"Polymers" as defined herein comprise copolymers (including terpolymers) and homopolymers. Further, the term "polymers" comprises both oligosaccharides and polysaccharides.

"Protected" as defined herein means that the at least one keratinous fiber demonstrated a greater degree of preservation of the α-structure and the tensile strength.

"Repairing" as used herein means that the at least one damaged keratinous fiber demonstrated an increase in α-structure and/or tensile strength following treatment of the at least one damaged keratinous fiber with the compositions of the invention.

It is to be understood that both the foregoing general description and the following detailed description are exemplary and explanatory only and are not restrictive of the invention, as claimed.

Figure 1:
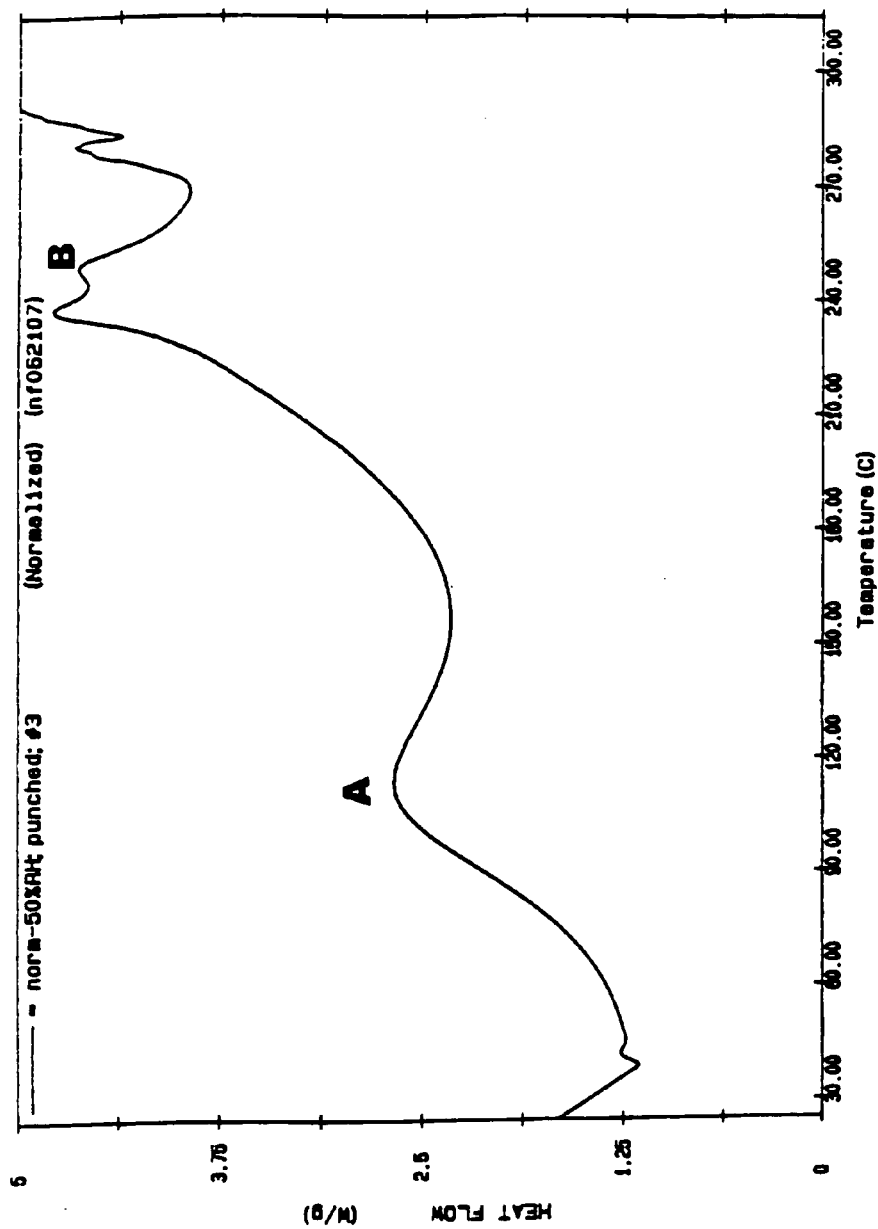
FIG. 1: A DSC (Differential Scanning Calorimetry) thermogram of normal brown hair. The hair sample was heated from 25° C. to 300° C. at a heating rate of 20° C./min. Peak A is the water release peak. Doublet peak B corresponds to the melting or rearrangement of the α-structure and its matrix contribution.

Reference will now be made in detail to exemplary embodiments of the present invention.

As described above, sugars have been used in hair care compositions and other treatments for their moisture retaining properties. However, it was unexpectedly discovered by the present inventors that, in addition to retaining moisture, a certain class of sugars provided protection to keratinous fibers from at least one type of extrinsic damage and also repaired keratinous fibers damaged by such extrinsic conditions. In particular with respect to hair, compounds comprising at least one $C_5$ to $C_7$ saccharide unit substituted with at least one amino group were found to protect the α-structure of the hair cortex. This is particularly true when the compounds are applied to the hair, and then the hair is heated.

Thus, the invention provides methods for protecting at least one keratinous fiber from extrinsic damage or for repairing at least one keratinous fiber following extrinsic damage comprising applying to the at least one keratinous fiber a composition comprising at least one compound comprising at least one $C_5$ to $C_7$ saccharide unit substituted with at least one amino group, and heating the at least one keratinous fiber. The composition may be applied to the at least one keratinous fiber prior to and/or during the heating of the at least one keratinous fiber. Further, the at least one compound is present in an amount effective to protect the at least one keratinous fiber from extrinsic damage or to repair the at least one keratinous fiber, depending on the embodiment. In one embodiment, the composition both protects the at least one keratinous fiber from extrinsic damage and repairs the at least one damaged keratinous fiber. The composition may further comprise at least one additional sugar.

The present invention also provides compositions for protecting at least one keratinous fiber from extrinsic damage or for repairing at least one keratinous fiber following extrinsic damage comprising at least one compound comprising at least one $C_5$ to $C_7$ saccharide unit substituted with at least one amino group. The at least one compound is present in an amount effective to protect the at least one keratinous fiber from extrinsic damage or to repair the at least one keratinous fiber, depending on the embodiment. In one embodiment, the composition is heat-activated. In another embodiment, the composition both protects the at least one keratinous fiber from extrinsic damage and repairs the at least one damaged keratinous fiber. The composition may further comprise at least one additional sugar.

Not to be limited as to theory, but, as described above, the mechanical properties of the hair are determined by the cortex, wherein coiled protein molecules are arranged in a specific and highly organized pattern (the "α-structure") representing a degree of crystallinity in the hair fiber. As the α-structure is sensitive to extrinsic conditions, the extent of damage to the hair by extrinsic conditions can be monitored by monitoring changes in the α-structure.

In addition to X-ray diffraction, which allows one to determine the presence of a crystalline structure in the material, one may determine a relative amount of crystallinity in the material by employing a much simpler method called differential scanning calorimetry (DSC). DSC is based on the fact that all materials have an ability to absorb a certain amount of energy on heating, and this amount of energy is sensitive to changes in the structure, phase, and composition of the material. For example, the amount of energy a material absorbs may change when a material undergoes a change in crystal structure, a phase transition, such as melting, or the loss of water.

In DSC, a small sample of material is sealed in a cell and the material is heated at a steady rate. The power required to achieve a certain temperature in the sample is compared to the power required to achieve the same temperature in the empty cell, which serves as a reference. The difference in the amount of heat input between the reference and the sample is recorded as a function of temperature. In the absence of phase transitions in the sample, there should be no change in heat input to maintain a constant temperature.

However, the amount of energy needed to maintain the temperature changes when the material undergoes a change in crystal structure, a phase transition, or the loss of water. For example, in a case where the material loses water, the water loss is an endothermic process, i.e., it requires energy. Therefore, the sample will absorb more energy as compared to the reference in order for the sample to remain at the same temperature as the reference. This process will be registered as an increase in the heat flow above the baseline in the form of a peak. The more water contained in the sample, the greater the peak area.

For example, it is well known that water plays an important role in physico-chemical properties of the keratin fibers. The moisture content in dry fibers depends on both the relative humidity of the environment and on the condition of the hair. The water in the hair fiber can exist in three forms: 1) water adsorbed strongly on binding sites, 2) water adsorbed weakly on binding sites, and 3) loosely bound or free water. Based on the values for the heat of hydration found for each of the groups, it can be speculated that strongly bound binding sites include amino groups (hydration heat of 16.8 kcal/mole), while weakly bound binding sites may include hydroxyl and carboxylic groups (5.7 kcal/mole and 7.4 kcal/mole, respectively).

Using DSC, one can observe the loss of water due to exposure of the hair to heat. The loosely bound and free water should be removed around 100° C., while the release of the strongly bound water should be observed above 140° C. In the DSC of keratinous fibers, a broad endotherm is observed from 75° C. to 200° C., which is initially related to removal of the free water, and then to the removal of more strongly bound water (See FIG. 1).

In a similar way, if a melting process or any other change in the crystal structure takes place in the sample, it requires additional energy, and thus will be manifested in the form of a peak on the DSC curve. The greater the degree of crystallinity or organized structure in the sample, the greater the peak area that will be observed. Therefore, DSC is also an excellent tool for observing the change in the α-structure of keratinous fibers and can help indicate hair damage.

From 20% to 30% of the hair cortex occurs in a highly organized (α-helical) form. Milczarek et al, *Colloid Polym. Sci.*, 270, 1106-1115 (1992). When the hair is heated above 230° C., a doublet peak is usually observed in DSC, which has been interpreted in terms of a first peak corresponding to the helix melting points (microfibrillar origin) and a second peak corresponding to cystine decomposition (matrix origin). Spei and Holzem, *Colloid & Polymer Sci.* 265, 965-970 (1987). However, further studies have shown that the first peak of the doublet, the microfibrillar peak, is more specifically a helix unfolding, superimposed by various decomposition reactions. Id. Herein, the term α-structure is associated with the doublet peak or peak area though technically the doublet area includes both a crystalline (microfibrillar) and non-crystalline (matrix) contribution. The α-structure represents the overall integrity of the fiber in an unstressed state. (See FIG. 1).

The greater the peak area, usually expressed in Joules per gram of hair, the higher the percentage of the hair cortex in the α-structure form. The DSC peak, at 210-250° C., also coincides with the disappearance of the alpha-pattern in the X-ray diffraction. Sandhu and Robbins, *J. Soc. Cosmet. Chem.*, 44, 163-175 (1993). In other words, when normal hair is damaged by heat, chemical treatment, or UV irradiation, a decrease in the doublet peak area of the DSC is observed and the amount of damage can be quantified by the peak area. The correlation between a decrease in DSC peak area and damage to the hair fibers is further verified by a corresponding decrease in the number of disulfide bonds (expressed as half-cystine) in the hair (see Table 1 below). A decrease in the number of disulfide bonds corresponds to a breakdown in the chemical structure of the hair.

TABLE 1

Effect of Chemical Treatment, Heat, and UV Irradiation on Chemical and Physical Properties of the Hair

| Hair type | Doublet peak area (J/g hair) | Half-Cystine (micromole/g hair) |
|---|---|---|
| Normal blonde hair | 81.57 +/− 8.28 | 918.7 +/− 165.8 |
| Blonde hair after: | | |
| Perm | 54.63 +/− 25.78 | 810.1 +/− 135.9 |
| Bleach | 53.22 +/− 13.12 | 740.1 +/− 45.9 |
| UV (180 h) | 13.98 +/− 11.78 | 629.7 +/− 8.8 |
| Heat (12 cycles at 130° C.)* | 18.63 +/− 8.56 | 654.3 +/− 50.7 |

*12 cycles, 1 min. each, at 130° C.

The detrimental changes in the chemical composition and in the amount of the hair crystallinity are also accompanied by cuticle loss and/or a decrease in the tensile strength. Shown in Table 2 below is the correlation between the doublet peak area and the wet tensile strength of normal and damaged hair. The wet tensile strength is expressed as the work required to stretch the wet fiber to 25% of its original length.

TABLE 2

Correlation between the Doublet Peak Area and the Wet Tensile Strength of Normal and Damaged Hair

| Hair type | Doublet Peak Area (J/g hair) n = 5 DSC tests | Work 25% (J/m$^2$) n = 100 fibers |
|---|---|---|
| Normal blonde hair | 25.00 +/− 4.90 | 555.0 +/− 122 |
| Blonde hair after: | | |
| Heat (12 cycles at 130° C.)* | 8.39 +/− 0.72 | 370 +/− 138 |
| Bleach | 6.90 +/− 0.55 | 222 +/− 93 |

*12 cycles, 1 min. each, at 130° C.

The above demonstrates that damage to the hair involves a decrease in the percentage of the hair cortex in the α-structure form. The inventors have found, however, that the damage to the α-structure can be prevented or at least lessened if the hair is treated with a composition comprising at least one compound comprising at least one $C_5$ to $C_7$ saccharide unit (Nomenclature: $C_5$-pentose, $C_6$-hexose, $C_7$-heptose) substituted with at least one amino group. The composition may be applied prior to and/or during heating of the keratinous fibers.

The present invention is thus also drawn to compositions for protecting at least one keratinous fiber from extrinsic damage and/or for repairing at least one keratinous fiber following extrinsic damage comprising at least one compound comprising at least one $C_5$ to $C_7$ saccharide unit substituted with at least one amino group. In one embodiment, the composition is heat-activated.

$C_5$ to $C_7$ saccharide units substituted with at least one amino group may also reduce cuticle loss and/or facilitate repair or re-building of the α-structure of the fibers following damage from extrinsic conditions. Although the inventors do not intend to be limited as to theory, the ability of these compounds comprising at least one $C_5$ to $C_7$ saccharide unit substituted with at least one amino group to repair keratinous fibers may be due to a reaction between the hair and the at least one $C_5$ to $C_7$ saccharide unit substituted with at least one amino group. When hair was treated with a composition comprising at least one $C_5$ to $C_7$ saccharide unit substituted with at least one amino group prior to heat application, changes in the chemical composition of the hair were observed. More specifically, the amount of lysine and arginine decreased, indicating what appears to be a Schiff base reaction between the aldehyde groups of the saccharide units and the amine groups of the hair fibers.

The at least one $C_5$ to $C_7$ saccharide unit according to the present invention may be chosen from any pentose, hexose and heptose. Further, the at least one $C_5$ to $C_7$ saccharide unit can be chosen from their D-form, L-form and mixtures of any of the foregoing. Non-limiting examples of $C_5$ to $C_7$ saccharide units are aldopentoses (such as xylose, arabinose, lyxose, and ribose), ketopentoses (such as ribulose and xylulose), aldohexoses (such as glucose and galactose), ketohexoses (such as fructose and sorbose), and heptoses (such as aldoheptoses and ketoheptoses, e.g., galactoheptulose and glucoheptulose). The at least one $C_5$ to $C_7$ saccharide unit may be chosen from those comprising aldehyde groups (aldoses), furanoses and other ring structures. The at least one $C_5$ to $C_7$ saccharide unit may be further substituted with at least one group different from the at least one amino group.

Derivatives of $C_5$ to $C_7$ saccharide units may also be used as the at least one $C_5$ to $C_7$ saccharide unit in the present invention. For example, ammonias or primary amines may react with the aldehyde or ketone group of a saccharide unit to form an imine derivative (i.e. a compound containing the functional group C=N). These imine compounds are sometimes also referred to as Schiff bases. Other non-limiting examples of derivatives of $C_5$ to $C_7$ saccharide units are hemiacetal derivatives of $C_5$ to $C_7$ saccharide units, hemiketal derivatives of $C_5$ to $C_7$ saccharide units and any oxidized derivatives of $C_5$ to $C_7$ saccharide units. These derivatives may be formed, for example, from the reaction of the aldehyde or ketone group of a saccharide unit with an alcohol. As previously mentioned, the at least one $C_5$ to $C_7$ saccharide unit may be further substituted with at least one group different from the at least one amino group. Thus, in one embodiment, the derivatives of $C_5$ to $C_7$ saccharide units may be further substituted with at least one group different from the at least one amino group.

According to the present invention, the at least one amino group may be chosen from substituted and unsubstituted amino groups. For example, the at least one amino group may be chosen from N-acetyl amino groups.

Further, the at least one $C_5$ to $C_7$ saccharide unit may be substituted with the at least one amino group at any position on the saccharide unit. For example, in one embodiment, the at least one $C_5$ to $C_7$ saccharide unit is substituted with the at least one amino group at the C1 position of the at least one $C_5$ to $C_7$ saccharide unit. In another embodiment, the at least one $C_5$ to $C_7$ saccharide unit is substituted with the at least one amino group at the C2 position of the at least one $C_5$ to $C_7$ saccharide unit.

Non-limiting examples of the at least one compound include $C_5$ monosaccharides substituted with at least one amino group, $C_6$ monosaccharides substituted with at least one amino group, $C_7$ monosaccharides substituted with at least one amino group, polymers comprising at least one $C_5$ monosaccharide substituted with at least one amino group, polymers comprising at least one $C_6$ monosaccharide substituted with at least one amino group, polymers comprising at least one $C_7$ monosaccharide substituted with at least one amino group, and glycoproteins comprising at least one $C_5$ to $C_7$ saccharide unit substituted with at least one amino group. In one embodiment, the at least one compound is chosen from oligosaccharides derived from the at least one $C_5$ to $C_7$ saccharide unit substituted with at least one amino group which may be further substituted with at least one group different from the at least one amino group.

Non-limiting examples of $C_5$ monosaccharides substituted with at least one amino group are pentosamines. In one embodiment, the pentosamines are chosen from aldopentosamines and ketopentosamines (such as xylosamine, arabinosamine, lyxosamine, ribosamine, ribulosamine and xylulosamine).

Non-limiting examples of $C_6$ monosaccharides substituted with at least one amino group include hexosamines (such as aldohexosamines and ketohexosamines). In one embodiment, for example, the hexosamines are chosen from glucosamine, galactosamine, allosamine, altrosamine, mannosamine, gulosamine, idosamine, galactosamine, and talosamine. In another embodiment, the at least one compound is glucosamine, and in another embodiment, is galactosamine.

Non-limiting examples of $C_7$ monosaccharides substituted with at least one amino group are heptosamines. For example, heptosamines may be chosen from aldoheptosamines and ketoheptosamines.

According to the present invention, the at least one compound comprising at least one $C_5$ to $C_7$ saccharide unit substituted with at least one amino group is present in the composition in an amount generally ranging from 0.01% to 10% by weight relative to the total weight of the composition, and in another embodiment from 0.1% to 5% by weight.

The compositions of the present invention as well as those of the inventive methods may further comprise at least one additional sugar which is different from the at least one compound comprising at least one $C_5$ to $C_7$ saccharide unit substituted with at least one amino group. The at least one additional sugar may, for example, aid in moisture retention. The effectiveness of a sugar in aiding in moisture retention may be measured by monitoring the DSC peak at a temperature ranging from 75° C. to 200° C.

The at least one additional sugar may be chosen from any sugar, carbohydrate and carbohydrate moiety. Non-limiting examples of the at least one additional sugar are monosaccharides, which include, but are not limited to, three to seven carbon sugars such as pentoses (for example, ribose, arabinose, xylose, lyxose, ribulose, and xylulose) and hexoses (for example, allose, altrose, glucose, mannose, gulose, idose, galactose, talose, sorbose, psicose, fructose, and tagatose); oligosaccharides such as disaccharides (such as maltose, sucrose, cellobiose, trehalose and lactose); and polysaccharides such as starch, dextrins, cellulose and glycogen. In one embodiment, the at least one additional sugar of the invention is chosen from any aldoses and ketoses. Further, the at least one additional sugar may be substituted or unsubstituted.

According to the present invention, the at least one additional sugar is present in the composition in an amount generally ranging from 0.01% to 10% by weight relative to the total weight of the composition, such as from 0.1% to 5% by weight.

The compositions of the present invention and those used in the methods of the present invention may be in the form of a liquid, an oil, a paste, a stick, a dispersion, an emulsion, a lotion, a gel, or a cream. Further, these compositions may further comprise at least one suitable additive chosen from additives commonly used in compositions for keratinous fibers. Non-limiting examples of the at least one suitable additive include anionic surfactants, cationic surfactants, nonionic surfactants, amphoteric surfactants, fragrances, penetrating agents, antioxidants, sequestering agents, opacifying agents, solubilizing agents, emollients, colorants, screening agents (such as sunscreens and UV filters), preserving agents, proteins, vitamins, silicones, polymers such as thickening polymers, plant oils, mineral oils, synthetic oils and any other additive conventionally used in compositions for the care and/or treatment of keratinous fibers.

Needless to say, a person skilled in the art will take care to select the at least one suitable additive such that the advantageous properties of the composition in accordance with the invention are not, or are not substantially, adversely affected by the addition(s) envisaged.

The compositions of the present invention and those used in the methods of the present invention may also be provided as one-part compositions comprising at least one compound comprising at least one $C_5$ to $C_7$ saccharide unit substituted with at least one amino group and, optionally, at least one additional sugar, or in the form of a multi-component treatment or kit. The skilled artisan, based on the stability of the composition and the application envisaged, will be able to determine how the composition and/or multicomponent compositions should be stored and mixed. For example, simple sugars such as $C_5$ to $C_7$ monosaccharides are known to be stable at pH levels ranging from 4 to 9. In compositions where the pH range is below or above these levels, the sugars would be stored separately and added to the composition only at the time of application.

Thus, the present invention also relates to a kit for protecting at least one keratinous fiber from extrinsic damage or for repairing at least one keratinous fiber following extrinsic damage comprising at least one compartment, wherein a first compartment comprises a first composition comprising at least one compound comprising at least one $C_5$ to $C_7$ saccharide unit substituted with at least one amino group. In one embodiment, the first composition further comprises at least one additional sugar, different from the at least one compound.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result.

EXAMPLES

Example 1

Effect of UV/Thermal History on the Structure of "Virgin" (Chemically Non-treated) Hair A swatch of Caucasian hair, dark blonde, coarse and wavy, 5 inches long and cut from the root, was tested. The hair had never been treated in any way that would cause changes in its chemical composition such as perming, relaxing, or coloring. The hair had only been subject to shampoo, conditioner (including oil treatment), styling aids, and blow drying, as well as the normal conditions of nature.

The swatch was divided into two sections, each 2.5 inches in length. For the DSC experiments, three samples of finely cut hair was accurately taken from the following parts of the swatch:

the extreme root end the 2.5 inch length, and the 5.0 inch length.

In the DSC experiments (using DSC-6 with Autosampler, Perkin Elmer), the hair was cut in small fragments (1-2 mm) and sealed in 40 ml aluminum pans that were punctured prior to heating, resulting in a 50 micron laser-drilled opening in the pan lid. The hair was heated from 25° C. to 300° C. at a heating rate of 20° C./min. Three runs per section were performed. The results were averaged and standard deviations determined.

The two sections were also tested for wet tensile strength using the fiber tensile testing instrument Dia-Stron (50 fibers per test). The following parameters were determined: Young's Modulus (the spring constant, measured in $N/m^2$); Work to stretch the hair fiber 25% of its length ($J/m^2$); Extension to Break (how far hair can be stretched before breaking, measured in % of hair length); Work to Break ($J/m^2$).

The DSC results are presented in Table 3, and the Dia-Stron data in Table 4. In both tables, the extreme root part of the hair is taken as the zero point. These results show the intrinsic loss of α-structure in hair due to normal conditions, i.e., they illustrate how the damage is greater the further you go from the root.

TABLE 3

Alpha-structure of Normal Hair as a Function of the Hair Length

| Hair Length, inches | Doublet Peak Area, J/g hair |
|---|---|
| 0 | 37.75 +/− 5.91 |
| 2.5 | 27.28 +/− 10.70 |
| 5.0 | 21.36 +/− 7.36 |

TABLE 4

Wet Tensile Strength of Normal Hair as a Function of the Hair Length

| Hair Length, inches | Young's Modulus, $MN/m^2$ | Work 25% $J/m^2$ | Break % | Work to Break $J/m^2$ |
|---|---|---|---|---|
| 0 to 2.5 | 732 +/− 114 | 395 +/− 103 | 60.3 +/− 4.3 | 1690 +/− 442 |
| 2.5 to 5.0 | 613 +/− 116 | 230 +/− 49 | 58.8 +/− 8.6 | 1100 +/− 232 |

Example 2

Effects of Amino Monosaccharides on The Tensile Strength of Relaxed Hair

Normal brown hair was processed with Revlon Realistic Professional Extra-Strength Relaxer for 30 min. at standard room temperature and humidity. The relaxed brown hair was subjected to six heat cycles, each heat cycle comprised applying the treatment solutions to the hair, blow-drying the hair, and applying heat to the hair for 1 min. in the form of the Professional Flat Iron (Solid Gold) set at "High" (130° C. to 135° C.). The hair was shampooed with a 10% solution of sodium laureth sulfate after each heat cycle, that is, after the heat application and prior to application of the treatment solution.

The treatment solutions included: a) deionized water; and b) 1% (w/v) glucosamine hydrochloride (Glucosamine HCl).

The hair was tested for wet tensile strength using a Dia-Stron. The fibers were stretched in water at a rate of 10 mm/min., with 50 fibers per test. The results were averaged, and standard deviations determined.

As used herein, "Young's modulus" corresponds to the initial resistance of the hair to the applied pulling force, "Work 25%" is the work required to extend the hair fiber to 25% of its length, "Break Extension" is the hair extension observed at the breaking point expressed at percent of its original length, and "Work-Break" is the work required to break the hair. The results are shown in Table 5.

The results show that hair treated with a 1% glucosamine hydrochloride solution demonstrated superior tensile properties, as compared to the control treatment with deionized water.

Example 3

Thermal Protection of Relaxed Hair after 6 Heat Cycles

The hair swatches from Example 2 were studied by differential scanning calorimetry (DSC). In this example, the hair was equilibrated at standard room temperature and humidity for 24 hours prior to testing. The results are shown in Table 6.

TABLE 6

Increase in the Doublet Peak Area as a Result of Six Heat Cycles: Effect of 1% Glucosamine HCl

| Hair type | Doublet Peak Area (J/g hair) |
|---|---|
| Normal brown hair | 15.91 +/− 7.67 |
| Relaxed brown hair | 4.80 +/− 0.16 |
| Relaxed Hair after 6 heat cycles with: | |
| Deionized water | 3.79 +/− 0.20 |
| 1% Glucosamine HCl | 23.11 +/− 7.09 |

A significant increase in the doublet area was observed in the hair treated with 1% Glucosamine hydrochloride solution as compared to the control solution (deionized water).

TABLE 5

Wet Tensile Strength of Relaxed Hair after Six Heat Cycles (n = 50 fibers)

| Hair type/ Treatment | Young's Modulus $(MN/m^2)$ | Work 25% $(J/m^2)$ | Break Extension (%) | Work-Break $(J/m^2)$ |
|---|---|---|---|---|
| Normal brown hair | 897 +/− 123 | 341 +/− 100 | 55.20 +/− 4.03 | 1420 +/− 418 |
| Relaxed brown hair | 129 +/− 128 | 132 +/− 30 | 59.30 +/− 7.08 | 558 +/− 126 |
| Relaxed Hair after 6 cycles at 130° C. with: | | | | |
| Deionized water | 108 +/− 60 | 64 +/− 20 | 52.70 +/− 11.8 | 426 +/− 134 |
| 1% Glucosamine HCl | 613 +/− 196 | 419 +/− 111 | 55.10 +/− 4.77 | 1800 +/− 477 |

Example 4

Thermal Protection of Bleached Hair after 6 and 12 Heat Cycles

Normal brown hair was bleached using Redken Blonding Gels Clear with 40 volume (12% hydrogen peroxide). The hair was subject to a total of twelve heat cycles. The heat treatment was as described in Example 2. The heat-treated hair was tested by DSC (Perkin Elmer Pyris 1 DSC) as described in Example 1. The hair was tested after Cycles 6 and 12.

The treatment solutions included: a) deionized water, b) 0.001% (w/v) glucosamine hydrochloride solution, c) 0.010% (w/v) glucosamine hydrochloride solution, d) 0.100% (w/v) glucosamine hydrochloride solution, and e) 1.000% (w/v) glucosamine hydrochloride solution.

Three DSC runs per treatment were performed, the results were averaged, and standard deviations determined. The results are shown in Table 7.

TABLE 7

Increase in the Doublet Peak Area as a Result of Six and Twelve Heat Cycles: Effect of 0.001% to 1.000% Glucosamine HCl

| Hair type | Doublet Peak Area (J/g hair) |
|---|---|
| Normal brown hair | 25.61 +/− 9.82 |
| Bleached brown hair | 5.73 +/− 0.54 |
| Bleached Hair after 6 and 12 heat cycles with: | |
| Deionized water, 6 cycles | 12.07 +/− 0.92 |
| Deionized water, 12 cycles | 11.96 +/− 2.07 |
| 0.001% Glucosamine HCl, 6 cycles | 11.11 +/− 1.74 |
| 0.001% Glucosamine HCl, 12 cycles | 14.74 +/− 5.95 |
| 0.010% Glucosamine HCl, 6 cycles | 12.32 +/− 3.74 |
| 0.010% Glucosamine HCl, 12 cycles | 21.66 +/− 12.88 |
| 0.100% Glucosamine HCl, 6 cycles | 17.32 +/− 2.23 |
| 0.100% Glucosamine HCl, 12 cycles | 20.92 +/− 1.73 |
| 1.000% Glucosamine HCl, 6 cycles | 19.40 +/− 4.14 |
| 1.000% Glucosamine HCl, 12 cycles | 22.98 +/− 6.57 |

A significant increase in the doublet area was observed in the hair treated with the glucosamine hydrochloride solutions as compared to the control solution (deionized water).

Example 5

Effect of Galactosamine on Thermal Protection

Normal brown hair was bleached with Redken Blonde Dimensions Dust-Free Bleached mixed with 40 volume (12% hydrogen peroxide). The bleached hair was then subject to twelve heat cycles. The heat treatment was as described in Example 2.

The heat-treated hair was tested by DSC (Perkin Elmer Pyris 1 DSC) as described in Example 1. The treatment solutions included: a) deionized water, and b) 1.0% (w/v) galactosamine hydrochloride.

Five DSC runs per treatment were performed, the results were averaged and standard deviations found. The results are shown in Table 8.

TABLE 8

Increase in the Doublet Peak Area as a Result of Twelve Heat Cycles: Effect of 1% Galactosamine HCl

| Hair type | Doublet Peak Area (J/g hair) |
|---|---|
| Bleached brown hair | 35.10 +/− 7.00 |
| Bleached Hair after 12 heat cycles with: | |
| Deionized water | 32.84 +/− 3.67 |
| 1% Galactosamine HCl | 41.52 +/− 3.94 |

A significant increase in the doublet area was observed in the hair treated with 1% galactosamine hydrochloride solution as compared to the control solution (deionized water).

Example 6

Thermal protection after 12 Cycles Using an Amino Pentose (0.1 wt % D-Lyxosylamine)

Normal blonde hair was subjected to 12 heat cycles, as described in Example 2, using a 0.1 wt % solution of D-Lyxosylamine.

TABLE 9

Thermal Protection of Normal Blonde Hair with 0.1 wt % Lyxosylamine: 12 Heat Cycles

| Treatment | Doublet Peak Area, J/g hair |
|---|---|
| Normal blonde hair, no treatment | 13.51 +/− 4.06 |
| After 12 heat cycles: | |
| Deionized water | 8.48 +/− 1.09 |
| 0.1% D-Lyxosylamine | 11.49 +/− 3.56 |

The lyxosylamine solution protected the α-structure hair, as compared to the control solution (deionized water).

What is claimed is:

1. A composition for protecting at least one keratinous fiber from extrinsic damage or repairing at least one keratinous fiber following extrinsic damage comprising:
    at least one glucosamine, and
    at least one additional sugar, said at least one additional sugar being different from glucosamine and comprising at least one $C_5$ to $C_7$ saccharide unit substituted with at least one amino group, wherein said at least one additional sugar is chosen from monosaccharides and oligosaccharides,
    wherein said at least one glucosamine is present in an amount effective to protect said at least one keratinous fiber from said extrinsic damage or to repair said at least one damaged keratinous fiber.

2. A composition for protecting at least one keratinous fiber from extrinsic damage or repairing at least one keratinous fiber following extrinsic damage comprising:
    at least one compound comprising at least one $C_5$ to $C_7$ saccharide unit substituted with at least one amino group, wherein said at least one compound is chosen from polysaccharides, and at least one additional sugar, said at least one additional sugar being different from said at least one compound comprising at least one $C_5$ to $C_7$ saccharide unit substituted with at least one amino group and derivatives thereof, wherein said at least one additional sugar is unsubstituted, wherein said at least one compound is present in an amount effective to protect said at least one keratinous fiber from said extrinsic damage or to repair said at least one damaged keratinous fiber.

* * * * *